Figure 1:
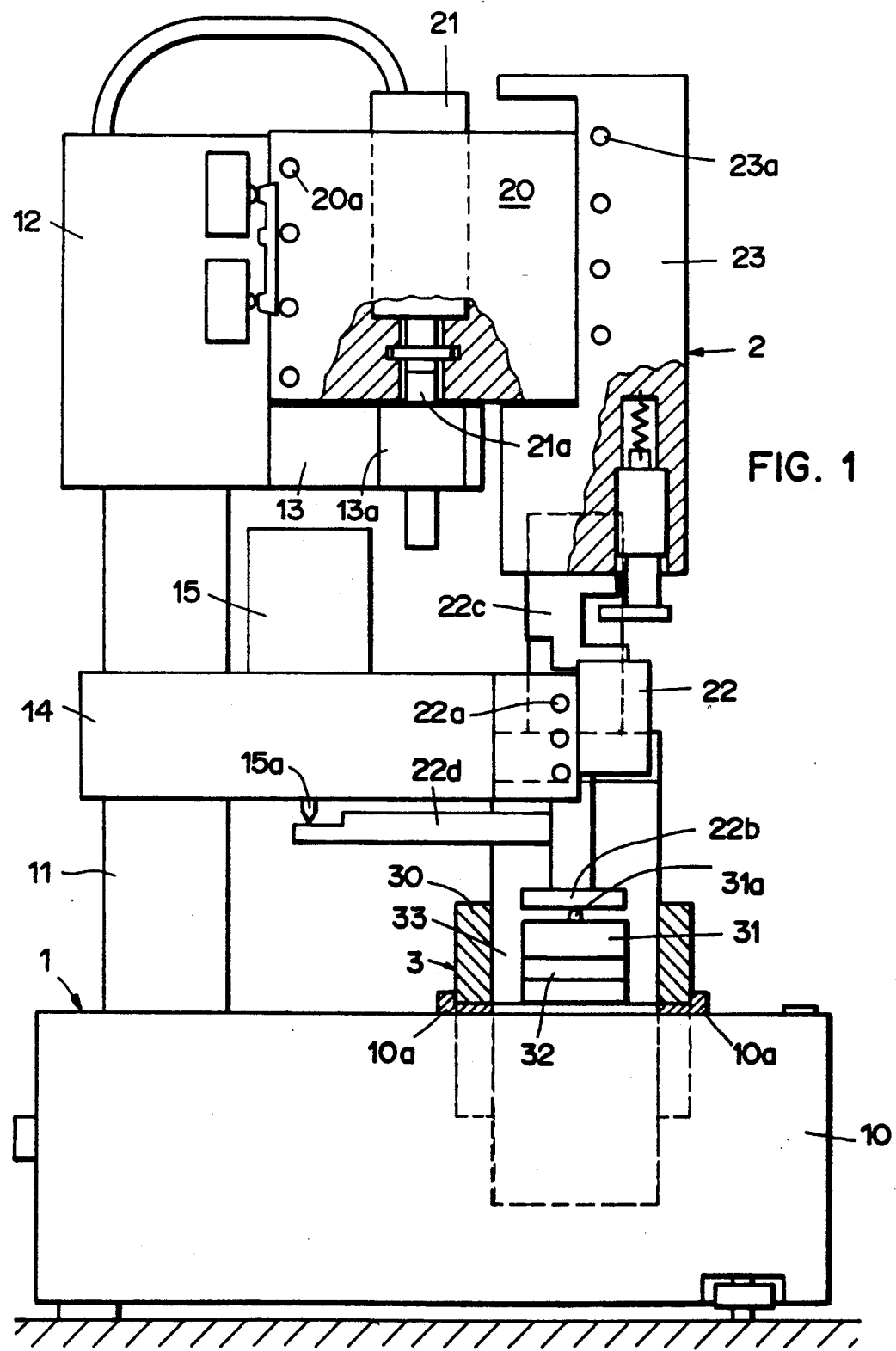

United States Patent [19]

Mussini et al.

[11] Patent Number: 5,142,917
[45] Date of Patent: Sep. 1, 1992

[54] APPARATUS AND METHOD FOR CHECKING MOVEMENT

[75] Inventors: Gian P. Mussini, St. Imier, Switzerland; Charles T. Higgins, Richmond, Va.

[73] Assignee: Fabriques de Tabac Reunies, S.A., Neuchatel, Switzerland

[21] Appl. No.: 714,033

[22] Filed: Jun. 12, 1991

[30] Foreign Application Priority Data

Jun. 20, 1990 [CH] Switzerland .................. 2059/90

[51] Int. Cl.$^5$ ............................................. G01N 3/08
[52] U.S. Cl. .......................................... 73/821; 73/9
[58] Field of Search ............. 73/1 B, 9, 818, 789, 73/790, 791, 792, 793, 821

[56] References Cited

U.S. PATENT DOCUMENTS 2,225,140 12/1940 Walker ............................ 73/9
4,090,393 5/1978 Kharitonov et al. ............. 73/1 B

FOREIGN PATENT DOCUMENTS 0195173 9/1986 European Pat. Off. .
WO8806271 8/1988 PCT Int'l Appl. .

Primary Examiner—Jerry W. Myracle
Attorney, Agent, or Firm—Jeffrey H. Ingerman

[57] ABSTRACT

An apparatus (3) is installed in place of a cigarette support, for example. The force applied by loads (22, 23) to a force-measurement cell (31), mounted on a motorized slider (33) and moving parallel to said loads, is measured as a function of the displacement. A processing unit plots a graph depicting the force measured as a function of the displacement; any imperfection of the surface condition of the slides (22a, 23a) can be spotted on the graph. The movement-checking method and apparatus apply to the checking of any rectilinear movement of a guided object subjected to a constant force, and particularly to the checking of the state of wear of the slides of equipment for measuring the compressibility of articles produced in the tobacco industry.

10 Claims, 3 Drawing Sheets

APPARATUS AND METHOD FOR CHECKING MOVEMENT

This invention relates to a method and apparatus for checking the regularity of the rectilinear movement of an object guided on a fixed support, such movement being caused by the application of a constant force to the object.

Equipment for checking the compressibility of articles of the tobacco industry, disclosed in European Patent Application Publication No. 0 195 173, has been developed and is currently in use. By means of this equipment the compressibility of a batch of cigarettes disposed in a suitable support is determined by measuring the vertical displacement of a constant load. When the load is applied, it moves vertically on two precision slides as the cigarettes are crushed. The precision and repeatability of the measurement depend, among other things, on the state of wear of the slides along which the load moves, for a worn slide, or one having a localized defect which does not permit regular and uniform displacement of the load, may lead to inaccuracies of measurement.

In order to avoid ambiguity of terms, the abovementioned equipment for checking the compressibility of articles in the tobacco industry will henceforth be called compressibility-measurement apparatus, the expression checking apparatus being reserved for the apparatus according to the present invention.

Checking the condition of the slides of the compressibility-measurement apparatus is not self-evident, for it is a question of reproducing the test conditions as faithfully as possible and of being sure that the parameters measured are indeed representative of the condition of the slides. In addition, the check must be reproducible, i.e., it must indicate the same defects during several successive tests on the same apparatus, and the results must be independent of the operator and of the place of testing. Finally, the check must be dynamic and must represent the condition of the slides in operation in the working zone at the time of the compressibility measurement.

A check carried out by substituting a spring for the support containing the cigarettes does not yield the desired results since the defects of the characteristic of the spring are added to those of the slides, which may be of the same order of magnitude. It is then difficult to distinguish between these two types of defects on the measurement graph. Likewise, when disposing a pasty object of known compressibility, the results obtained depend greatly upon the ambient conditions (temperature, humidity), as well as upon the aging of the paste, which means that it is difficult to compare two apparatuses in two different laboratories.

It is an object of this invention to provide an improved method and apparatus by means of which the foregoing shortcomings may be remedied.

To this end, in the checking method according to the present invention, the force applied to the object is measured as a function of the displacement of said object.

The checking apparatus according to the present invention for carrying out the foregoing method comprises a force-measurement cell mounted on a motorized slider, moving in the same direction as the object in movement, i.e., the constant load, the motorized slider imparting a regular rectilinear movement to the force-measurement cell.

The checking method and apparatus will be described as applied to checking the slides of equipment for measuring the compressibility of cigarettes, but it is to be understood that the method and apparatus apply just as well to other kinds of apparatus or machines comprising one or more slides on which an object moves under the effect of a constant force.

Figure 2:
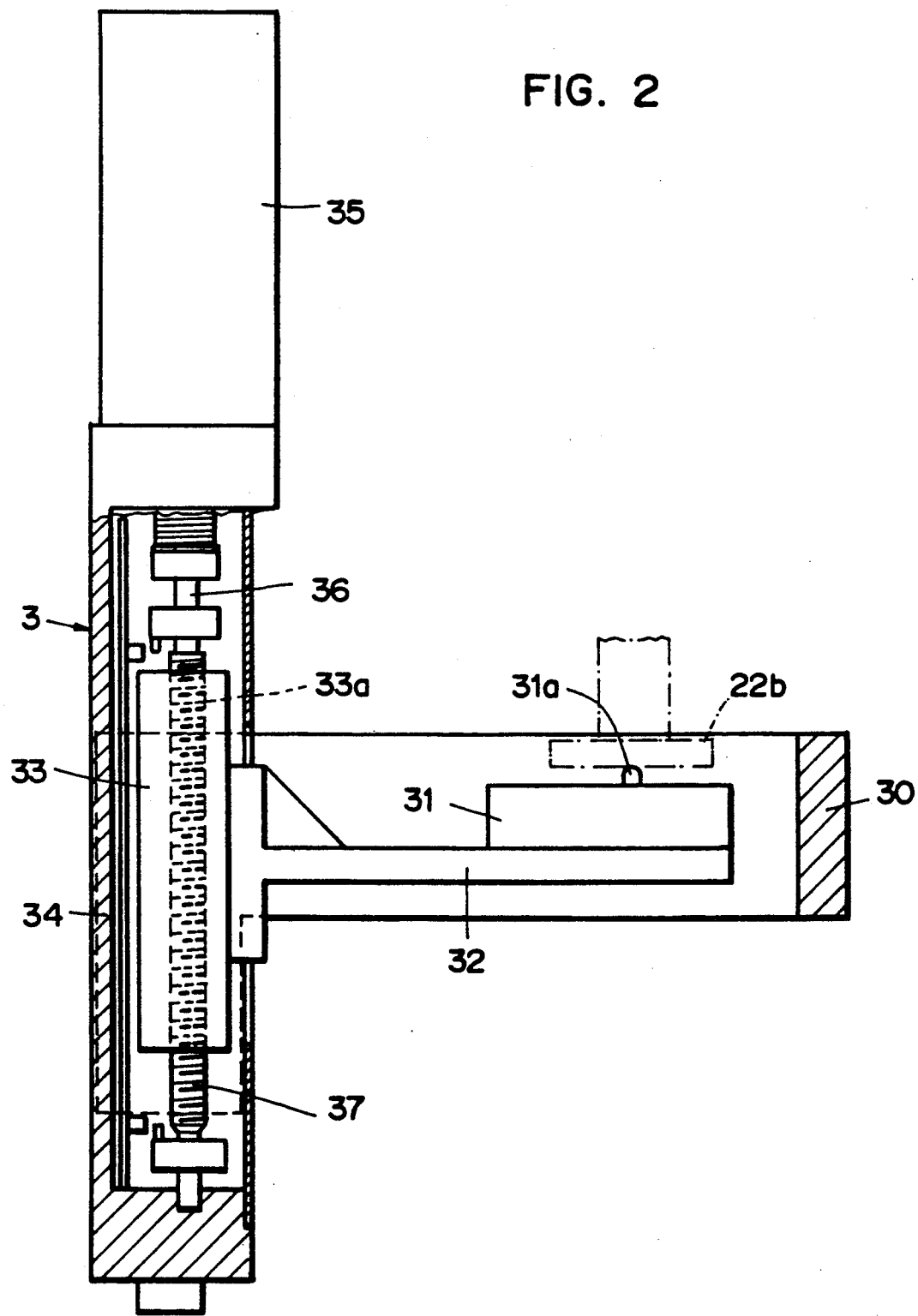
Figure 3A:
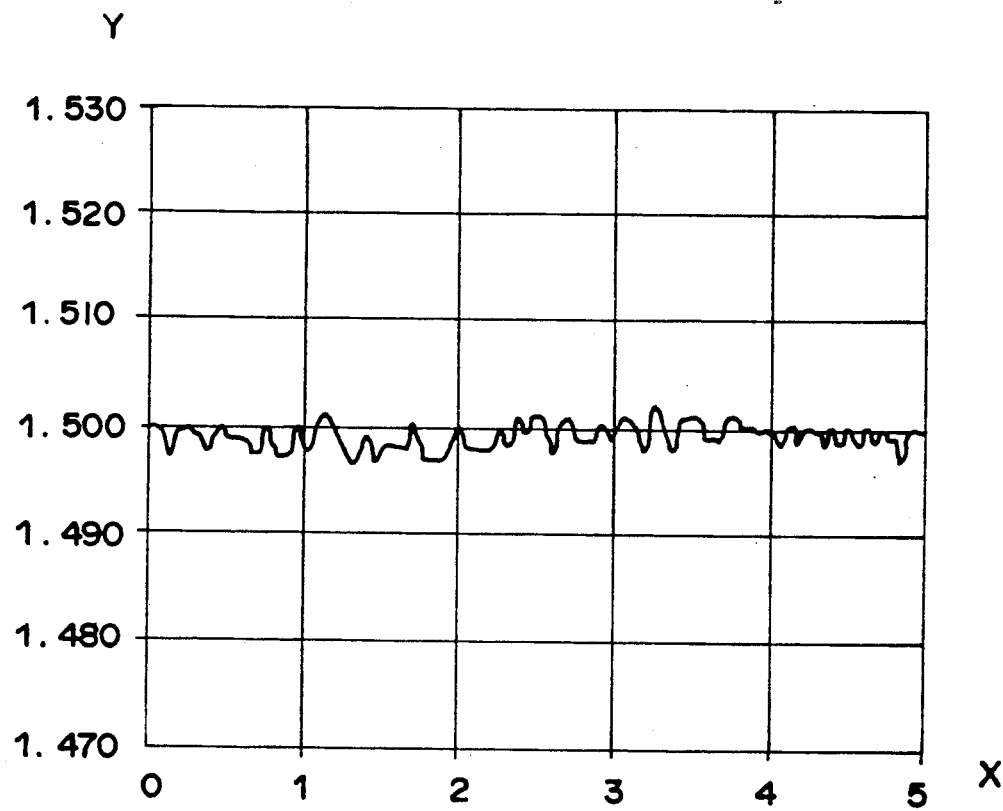
Figure 3B:
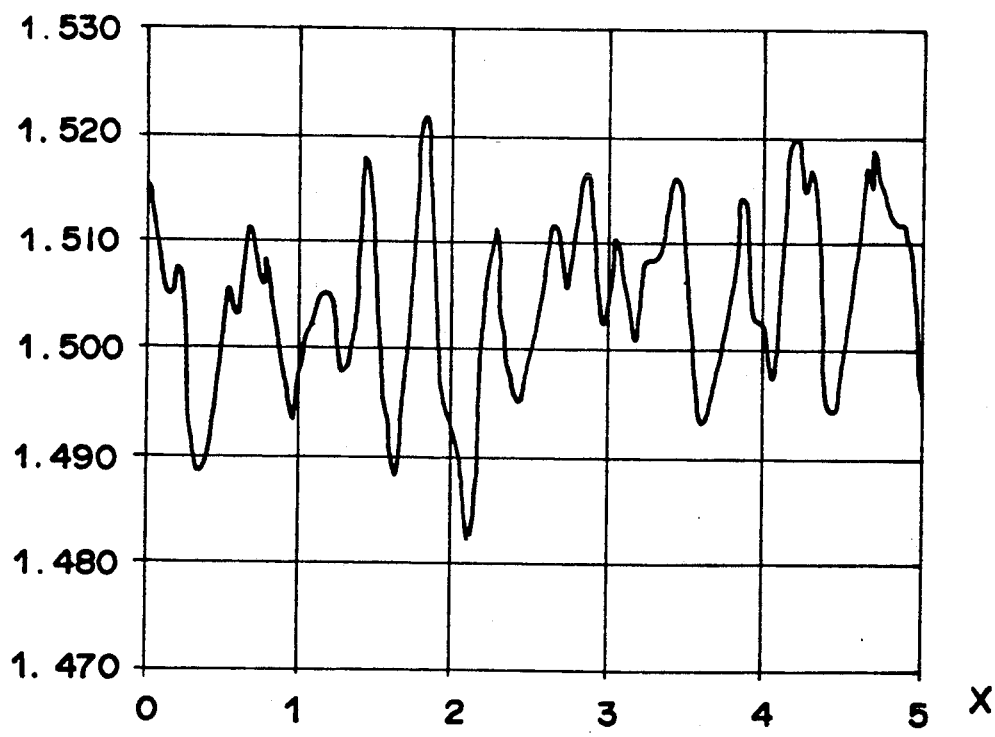

A preferred embodiment of the invention will now be described in detail with reference to the accompanying drawings, in which:

FIG. 1 is a front elevation, partially in section, of checking apparatus according to the invention placed on equipment for measuring the compressibility of cigarettes, FIG. 2 is a side elevation on a larger scale, also partially in section, of the apparatus according to the invention, and FIGS. 3A and 3B are graphs of recordings made during checks of slides in good condition and in poor condition, respectively.

Apparatus 1 for measuring the compressibility of cigarettes as shown in FIG. 1 is composed principally of a base 10, comprising guide rails 10a, of a vertical pillar 11, of an upper block 12 to which an upper arm 13 is fixed, and of an intermediate arm 14, which constitute the main fixed elements of the apparatus. The moving elements 2 are made up principally of a control block 20, capable of moving vertically relative to the upper block 12, through the action of the motor 21, the threaded spindle 21a of which is engaged in the nut 13a forming part of the upper arm 13. The sliding of the control block 20 on the upper block 12 takes place by means of the ball-bearing slide 20a. A first load 22, sliding vertically along the intermediate arm 14 via the ball-bearing slide 22a, comprises the pressing plate 22b acting upon the test object, as well as hooking and pressing means 22c connecting this first load 22 to the main load 23 which slides vertically along the control block 20 via the ball-bearing slide 23a. A lateral finger 22d, fixed to the first load 22, acts upon the point 15a of a comparator 15 in order to measure the vertical displacement of the pressing plate 22b. The other elements, as well as the operation of this apparatus for a compressibility measurement of cigarettes, are described in the patent application mentioned earlier; they need not be further described here. In order to ensure a correct and repetitive measurement of compressibility, it is essential that the loads 22 and 23 move regularly, without play and without jerking, along the slides 22a and 23a. The slide-checking apparatus 3 is placed on the base 10, its base support 30 of aluminum being guided by the guide rails 10a, in place of the support bearing the cigarettes of which the compressibility is to be measured.

The details of the make-up of the checking apparatus are more particularly visible in FIG. 2. The base support 30 is made up of a hollow frame of rectangular shape; the base surface of this support is machined with great precision so as to adapt itself exactly to the guide rails 10a in order that the rest of the elements of the checking apparatus 3 may be exactly positioned for carrying out their functions correctly. Within this rectangular frame forming base support 30, a force-measurement cell 31, which may preferably be an HBM Z11 cell, comprising a touch point 31a, is suspended on an angle-iron 32, rigidly connected in turn to a motorized slider 33. This slider 33 has a vertical movement and is guided with precision within a chassis 34; a DC motor 35, rotatingly actuating n one direction or the other the spindle 36 threaded at its end 37, drives the slider 33 with a straight vertical movement by means of a tapped portion 33a traversing said slider and fitted on the tapped end 37. Preferably, the motor 35, the chassis 34, and the slider 33 will be made up of a single precision element, e.g., a Micro-Controle motorized slider. Thus, by feeding the motor 35 with a positive or negative voltage, it is possible to rotate the spindle 36, i.e., its threaded portion 37, in one direction or the other, which through an effect of screwing or unscrewing of the tapped portion 33a of the slider 33 drives the latter with a vertical movement upward or downward, carrying along in the same movement the angle-iron 32 and the force-measurement cell 31.

The method, as well as the operation of the apparatus for checking the condition of the slides according to the invention, may now be described.

The compressibility-measurement apparatus is first of all brought into starting position, i.e., the control block 20 is brought into its uppermost position, the loads 22 and 23 being suspended there by their suitable suspension means. Seeing that the pressing plate 22b is thus in uppermost position as well, it is easy to withdraw the cigarette support and to introduce the checking apparatus 3 in its place on the base 10, guiding it via the guide rails 10a. By actuating the motor 35, the measurement cell is also brought into starting position, i.e., into its uppermost position, without, however, bringing the touch point 31a into contact with the pressing plate 22b, this in order to protect the measurement cell 31 and to avoid having too great a load applied to it. The control block 20 is now controlled downward, bringing the plate 22b into contact with the touch point 31a, which means that said touch point, hence the measurement cell, first of all supports the first load 22, then the main load 23, or a total mass of 1500 g. These loads are immobilized by the measurement cell 31 whereas the control block 20 continues its downward travel in order to disengage itself completely from the main load 23. The stopping position of the control block will be so chosen that at the time of the later descent of the load, the latter is never retained by said control block, and the control block does not press on the load. This position is that depicted in FIG. 1. Then a monitored voltage is applied to the motor 35, imparting to it an absolutely regular rotational movement, hence giving the slider 33 and the cell 31 an absolutely regular downward translational movement; the displacement of the plate 22b is measured by the comparator 15, supplying an electric signal proportional to said displacement, whereas the force applied by the plate 22b is measured by the measurement cell 31; these two electric signals are sent to a processing unit (not shown) which establishes a diagram representing the force measured as a function of the displacement. It is important that the slides be checked in any case in the zone in which the measurement of compressibility takes place; for this purpose, from the starting point mentioned above, the load is first of all lowered by about 1.8 mm, a location where the full scale of 1500 g is regulated; when the travel reaches 2 mm, the scale of the displacement is reset, then the measurement is taken of the force applied to the cell 31 as a function of the displacement measured by the comparator 15, this over 5 mm of travel. When the slider 33 has reached its lower position, the downward displacement of the apparatus is stopped, the control block 20 is controlled upward in order to lift the loads 22 and 23 from the measurement cell 31.

Examples of graphs obtained via the processing unit are depicted in FIGS. 3A and 3B, where on the X-axis there is the displacement measured by the comparator 15, from 0 to 5 mm, and on the Y-axis the load corresponding to a mass in grams measured by the cell 31 at the time of said displacement. A load measurement is made every $\mu$m, the average of five consecutive measurements being transferred to the graph. In the case where the displacement of the loads 22 and 23 along the slides 22a and 23a takes place without jerking, i.e., when said slides are in good condition, the values measured for the load deviate only very little from the nominal value of 1500 g corresponding to the total load; this case is shown in FIG. 3A, where the load variation is between $+2$ g and $-3$ g. In the case where irregularities or defects on one or the other of the slides 22a and 23a impart jerks to the displacement of the loads, a graph similar to that depicted in FIG. 3B is obtained, where the maximum load variation is from $+22$ g to $-18$ g. It is obvious that such variations in the measurement zone would completely falsify a compressibility measurement.

The aforementioned processing unit automatically or manually controls the various steps of the check, picks up the measurement signals, processes them, and plots the graph indicating the measurement. This control unit may be either separate from or associated with the control unit of the compressibility-measurement apparatus.

Thus, through the checking method and with the aid of the checking apparatus according to the invention, it is possible rapidly to check the quality of the slides of the compressibility-measurement apparatus in order to be sure that the indicated values of compressibility really correspond to the measured values. For this purpose, it is necessary to assume a limit value at the time of the check, for example $\pm 5$ g, beyond which the measurement apparatus is deemed defective, possibly after a second confirming check, and must be overhauled. A single checking apparatus may serve to check numerous compressibility-measurement apparatuses, whether these be installed in a single laboratory or in several laboratories which may be distant from one another; in other words, the checking of the slides is independent of the apparatus measured, as well as of the surrounding ambient conditions.

Such a method may be provided for the movement check of other types of measurement apparatus than that described; for example, a hardness-measurement device may also be tested by this method, a suitable checking apparatus being installed in place of the part to be measured. More generally, the regularity of displacement of any part having a rectilinear movement may be checked according to the method of the invention, on condition that this movement is caused by the application of a constant force to said part.

What is claimed is:

1. Apparatus for checking the steadiness of the rectilinear movement in a first direction of an object guided on a fixed support, said object being subject to a constant first force in said first direction causing said rectilinear movement and to a frictional force against said fixed support in a second direction opposite said first direction, said apparatus comprising:

a slider, a force-measurement cell mounted on said slider, and motor means for applying a third force for moving said slider in said first direction for imparting a steady rectilinear movement to said force-measurement cell.

2. The apparatus of claim 1, wherein:

said fixed support is a portion of a device for checking the compressibility of articles, said device including a second support for containing said articles, said apparatus further comprises a frame for inserting in said device in place of said second support, and said slider and said force-measurement cell are mounted in said frame.

3. The apparatus of claim 1, wherein said force-measurement cell is capable of transmitting first electric signals, further comprising a displacement-measurement comparator capable of transmitting second electric signals and control unit for controlling the checking operation, for actuating said slider, for receiving said first and second electric signals, for processing said signals, and for plotting a graph indicating the results of said checking operation.

4. The apparatus of claim 3, wherein the variation of the force measured as a function of the displacement of a load on one or more slides indicates the state of wear of said slide or slides.

5. Apparatus for checking the condition of vertical slides intended for rectilinear movement in a first direction of a constant load in equipment for measuring the compressibility of articles produced in the tobacco industry, said load being subject to a constant first force in said first direction causing said rectilinear movement and to a frictional force against said vertical slides in a second direction opposite said first direction, said apparatus comprising:

a slider, a force-measurement cell mounted on said slider, and motor means for applying a third force for moving said slider in said first direction for imparting a steady rectilinear movement to said force-measurement cell.

6. The apparatus of claim 5, wherein:

said equipment includes a support for containing said articles, said apparatus further comprises a frame for inserting in said equipment in place of said support, and said slider and said force-measurement cell are mounted in said frame.

7. The apparatus of claim 5, wherein said force-measurement cell is capable of transmitting first electric signals, further comprising a displacement-measurement comparator capable of transmitting second electric signals and control unit for controlling the checking operation, for actuating said slider, for receiving said first and second electric signals, for processing said signals, and for plotting a graph indicating the results of said checking operation.

8. The apparatus of claim 7, wherein the variation of the force measured as a function of the displacement of a load on one or more slides indicates the state of wear of said slide or slides.

9. A method of checking the regularity of the rectilinear movement in a first direction of an object guided on a fixed support, said object being subject to a constant force in said first direction causing said movement and being subject to a frictional force against said fixed support in a second direction opposite to said first direction, said method comprising the step of measuring the resultant of said constant force and said frictional force as a function of the displacement of said object along said fixed support.

10. The method of claim 9 applied to the checking of vertical slides intended for the movement of a constant load of apparatus for measuring the compressibility of articles produced in the tobacco industry.

* * * * *